(12) United States Patent
Li et al.

(10) Patent No.: US 11,980,351 B2
(45) Date of Patent: May 14, 2024

(54) DEVICE FOR VISIBLE PUNCTURE

(71) Applicant: Wuhan Youcare Technology Co., Ltd., Wuhan (CN)

(72) Inventors: Jianxing Li, Wuhan (CN); Jinping Li, Wuhan (CN); Chengpeng Liu, Wuhan (CN); Gang Long, Wuhan (CN); Yeyun Mao, Wuhan (CN); Xuecheng Hu, Wuhan (CN)

(73) Assignee: WUHAN YOUCARE TECHNOLOGY CO., LTD., Wuhan (CN)

(*) Notice: Subject to any disclaimer, the term of this patent is extended or adjusted under 35 U.S.C. 154(b) by 849 days.

(21) Appl. No.: 17/080,823

(22) Filed: Oct. 26, 2020

(65) Prior Publication Data

US 2021/0038250 A1 Feb. 11, 2021

Related U.S. Application Data

(63) Continuation-in-part of application No. PCT/CN2018/104295, filed on Sep. 6, 2018.

(30) Foreign Application Priority Data

Apr. 27, 2018 (CN) .......................... 201810395296.X

(51) Int. Cl.
*A61B 1/313* (2006.01)
*A61B 1/04* (2006.01)
(Continued)

(52) U.S. Cl.
CPC .............. *A61B 1/313* (2013.01); *A61B 1/044* (2022.02); *A61B 17/3415* (2013.01);
(Continued)

(58) Field of Classification Search
CPC ..... A61B 1/313; A61B 1/044; A61B 17/3415; A61B 17/3421; A61B 1/00165;
(Continued)

(56) References Cited

U.S. PATENT DOCUMENTS 4,315,512 A * 2/1982 Fogarty ............... A61M 25/104
604/103.11
11,376,037 B2 * 7/2022 Desjardin .......... A61B 17/3417
(Continued)

*Primary Examiner* — Jing Rui Ou
(74) *Attorney, Agent, or Firm* — MATTHIAS SCHOLL P.C.; Matthias Scholl

(57) ABSTRACT

A device for visible puncture includes a balloon, a canula, a needle tube, an image acquisition device, and a fluid injection tube. The balloon includes a first end including a first hole, and a second end including a second hole. The canula includes a first axial through hole. The needle tube includes a second axial through hole and is disposed in the first axial through hole. The image acquisition device is disposed in the second axial through hole. The balloon is axially disposed on the canula. The first end of the balloon is disposed on the outer wall of the front end of the needle tube, and the second end of the balloon is disposed on the outer wall of the front end of the canula. The second axial through hole includes a fluid channel disposed between the outer wall of the needle tube and the canula.

9 Claims, 4 Drawing Sheets

(51) Int. Cl.
 *A61B 17/34* (2006.01)
 *A61B 1/00* (2006.01)
(52) U.S. Cl.
 CPC ...... *A61B 17/3421* (2013.01); *A61B 1/00165* (2013.01); *A61B 17/34* (2013.01); *A61B 2017/3413* (2013.01); *A61B 17/3478* (2013.01); *A61B 2017/3486* (2013.01); *A61B 2217/007* (2013.01)
(58) Field of Classification Search
 CPC ...... A61B 2017/3413; A61B 2217/007; A61B 2017/3486; A61B 17/3478
 See application file for complete search history.

(56) References Cited

U.S. PATENT DOCUMENTS

| | | | | |
|---|---|---|---|---|
| 2005/0004522 | A1* | 1/2005 | Katoh | A61M 25/0084 604/164.01 |
| 2005/0228452 | A1* | 10/2005 | Mourlas | A61M 25/1002 606/41 |
| 2006/0004286 | A1* | 1/2006 | Chang | A61B 90/16 606/198 |
| 2009/0062872 | A1* | 3/2009 | Chin | A61B 1/00082 606/86 R |

* cited by examiner

DEVICE FOR VISIBLE PUNCTURE

CROSS-REFERENCE TO RELATED APPLICATIONS

This application is a continuation-in-part of International Patent Application No. PCT/CN2018/104295 with an international filing date of Sep. 6, 2018, designating the United States, now pending, and further claims foreign priority benefits to Chinese Patent Application No. 201810395296.X filed Apr. 27, 2018. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to a device for visible puncture.

A conventional device for puncture comprises a puncture needle, a guide wire, and a sheath. When in use, the puncture needle is first guided to, for example, renal pelvis or calyces of a patient, and then the needle core of the puncture needle is withdrawn. Observe whether there is a urine on the needle core to judge the success or failure of the puncture operation. If not, the puncture operation is repeated. If so, the needle core is removed and the sheath is inserted to produce a channel, and the guide wire is introduced to the operation site through the channel. Thereafter, the guide wire is stabilized, the sheath is withdrawn, and a balloon is introduced to the renal pelvis or calyces of the patient along the guide wire. The balloon is filled with normal saline via an external water injection tube and an external syringe. The use of the device is time-consuming, inefficient, and costly.

SUMMARY

The disclosure provides a device for visible puncture, the device comprising a balloon, a canula, a needle tube, an image acquisition device, and a fluid injection tube. The balloon comprises a first end comprising a first hole, and a second end comprising a second hole. The canula comprises a first axial through hole. The needle tube comprises a second axial through hole and is disposed in the first axial through hole. The image acquisition device is disposed in the second axial through hole. The balloon is axially disposed on the canula; the first end of the balloon is disposed on an outer wall of a front end of the needle tube, and the second end of the balloon is disposed on an outer wall of a front end of the canula; a rear end of the canula is in conjunction with the outer wall of the needle tube; the second axial through hole comprises a fluid channel disposed between the outer wall of the needle tube and an inner wall of the balloon, and between the outer wall of the needle tube and an inner wall of the canula. The fluid injection tube is connected to the fluid channel.

In a class of this embodiment, the device further comprises a water injection tube communicating with the second axial through hole; the image acquisition device comprises a first outer wall facing the water injection tube and a second outer wall back to back with the first outer wall; a first channel is disposed between an inner wall of the needle tube and the first outer wall of the image acquisition device; and the first channel communicates with the water injection tube.

In a class of this embodiment, the device further comprises an instrument delivery pipe communicating with the second axial through hole and facing the second outer wall; the water injection tube and the instrument delivery pipe are disconnected in the second axial through hole; a second channel is disposed between the inner wall of the needle tube and the second outer wall of the image acquisition device; and the second channel communicates with the instrument delivery pipe.

In a class of this embodiment, the device further comprises a handle; the rear end of the canula and a rear end of the needle tube are fixed in the handle; the handle comprises a first cylindrical holder, a second cylindrical holder coaxially fixed on the first cylindrical holder, and a tapered holder coaxially fixed on the second cylindrical holder; a diameter of the second cylindrical holder is larger than a diameter of the first cylindrical holder; a transition section of the second cylindrical holder and the tapered holder comprises a clamping part shaped like a finger; and the tapered holder comprises a rear end having an annular circumferential surface.

In a class of this embodiment, the fluid injection tube comprises a first front end fixed in the handle, and a first rear end comprising a first joint for fluid injection; the water injection tube comprises a second front end fixed in the handle, and a second rear end comprising a second joint for water injection; the instrument delivery pipe comprises a third front end fixed in the handle, and a third rear end comprising a third joint for instrument introduction; and the rear end of the needle tube is connected to a fourth joint communicating with the image acquisition device.

In a class of this embodiment, the image acquisition device comprises a first end fixed on the inner wall of the needle tube, and a second end passing through the fourth joint.

In a class of this embodiment, the balloon comprises a first welding part and a second welding part fixed on the outer wall of the front end of the needle tube and the outer wall of the front end of the canula, respectively.

In a class of this embodiment, the device further comprises a sheath disposed on the balloon; the sheath comprises a third axial through hole; when the balloon is filled with a fluid and expanded to show a maximum section width, and the maximum section width is smaller than an inner diameter of the sheath.

In a class of this embodiment, a radial section of the balloon is circular, and an axial section of the balloon comprises a rectangular center and two circular ends.

In a class of this embodiment, the front end of the needle tube comprises a tapered head; the tapered head comprises a tapered front end and a flat rear end; the tapered head further comprises a central hole communicating with the second axial through hole and the central hole has the same diameter as the second axial through hole; the first end of the balloon is fixed on the flat rear end of the tapered head, and an outer diameter of the flat rear end of the tapered head is the same as an outer diameter of the first end of the balloon.

Figure 1:
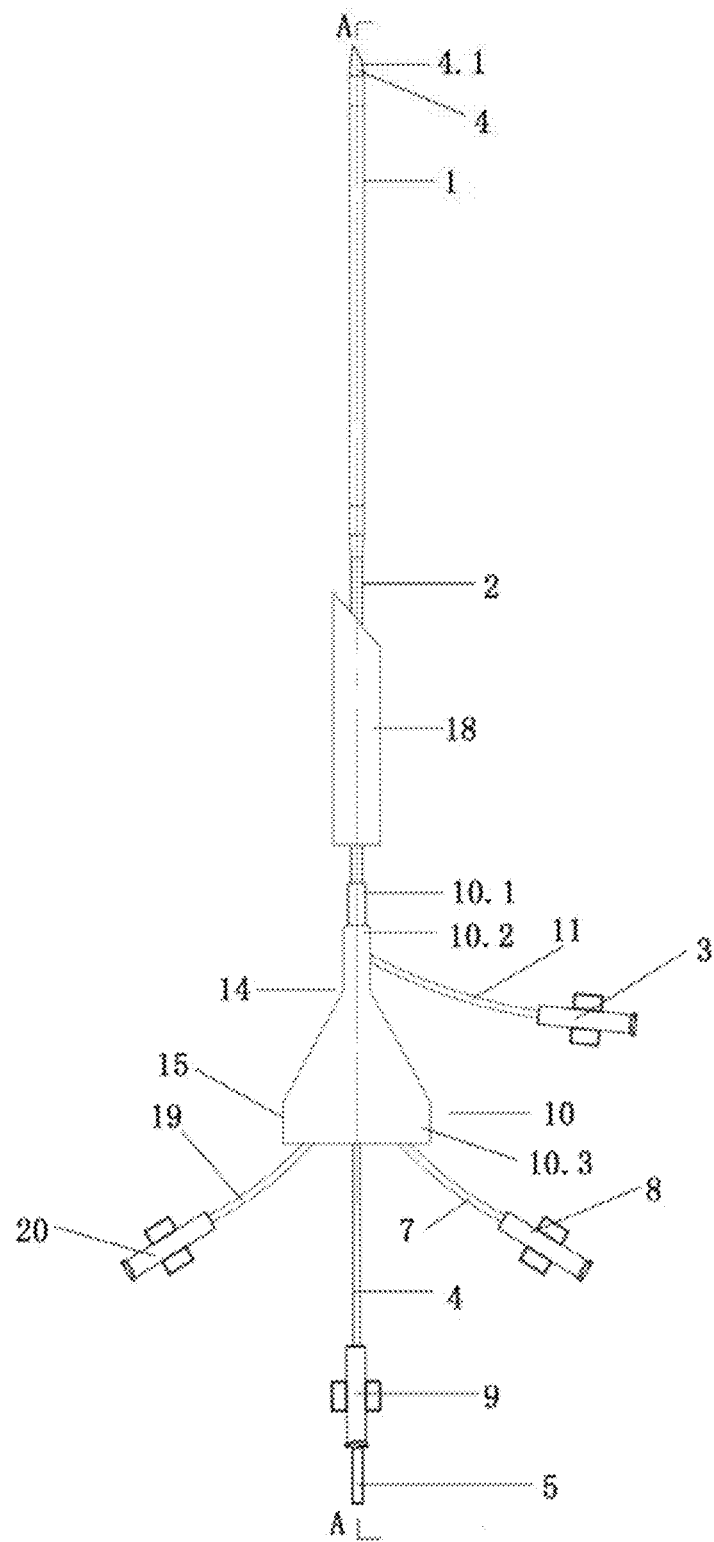
FIG. 1 is a top view of a device for visible puncture according to one embodiment of the disclosure.
Figure 2:
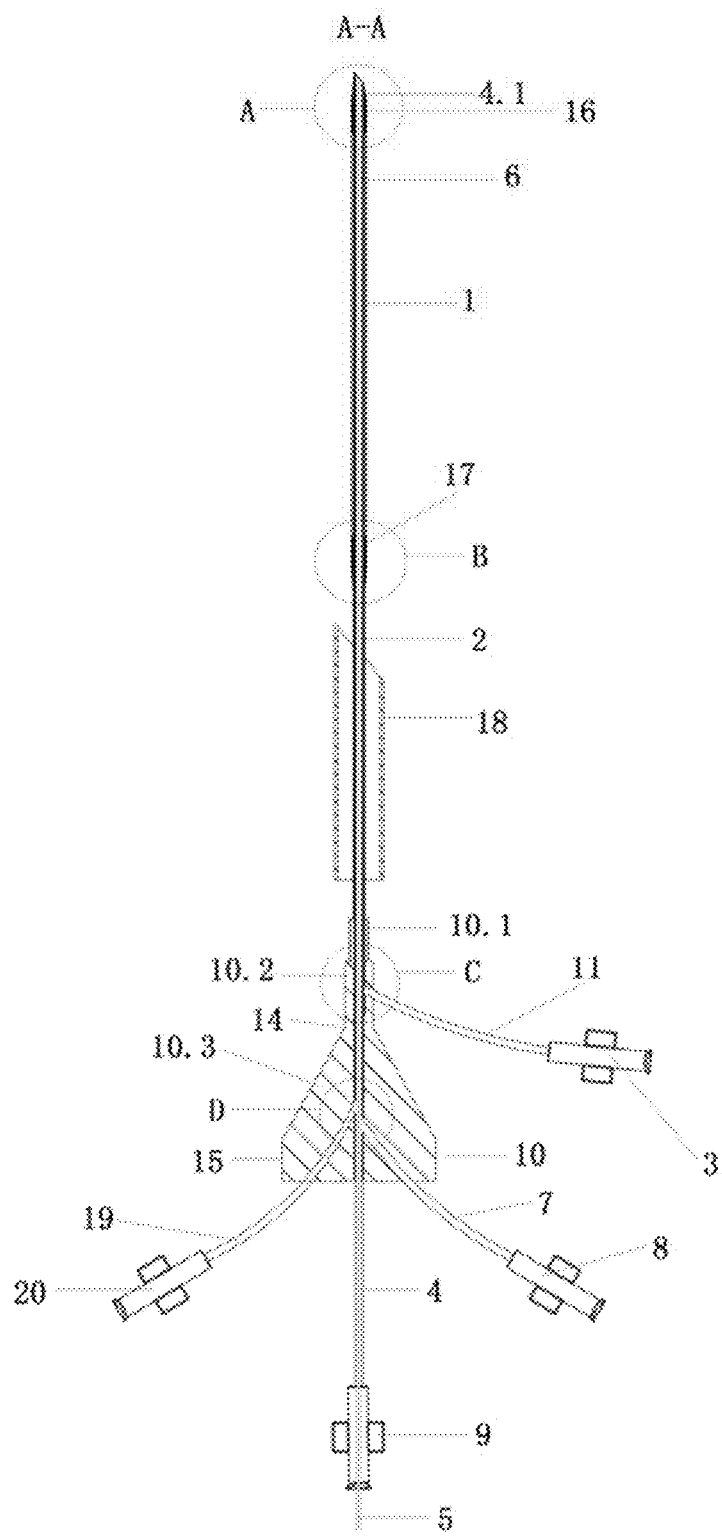
FIG. 2 is a sectional view taken from line A-A in FIG. 1.
Figure 3:
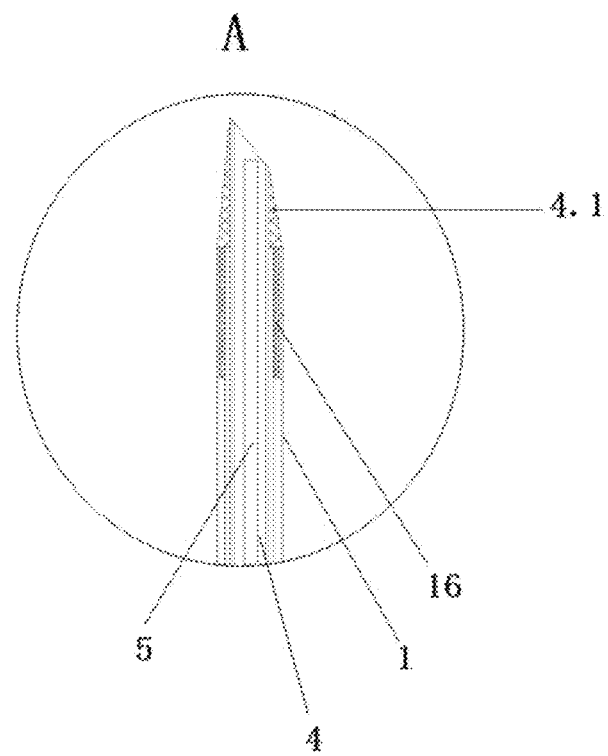
FIG. 3 is a local enlarged view of part A in FIG. 2.
Figure 4:
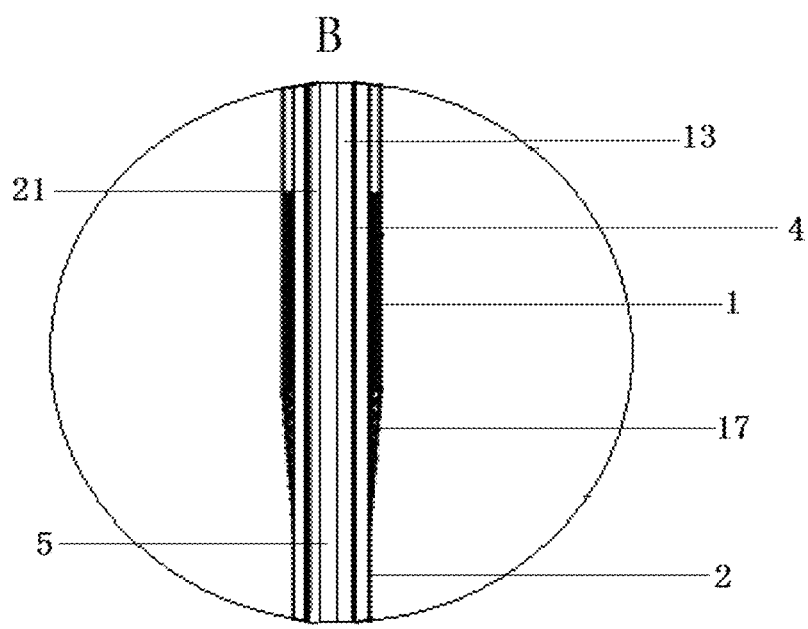
FIG. 4 is a local enlarged view of part B in FIG. 2.
Figure 5:
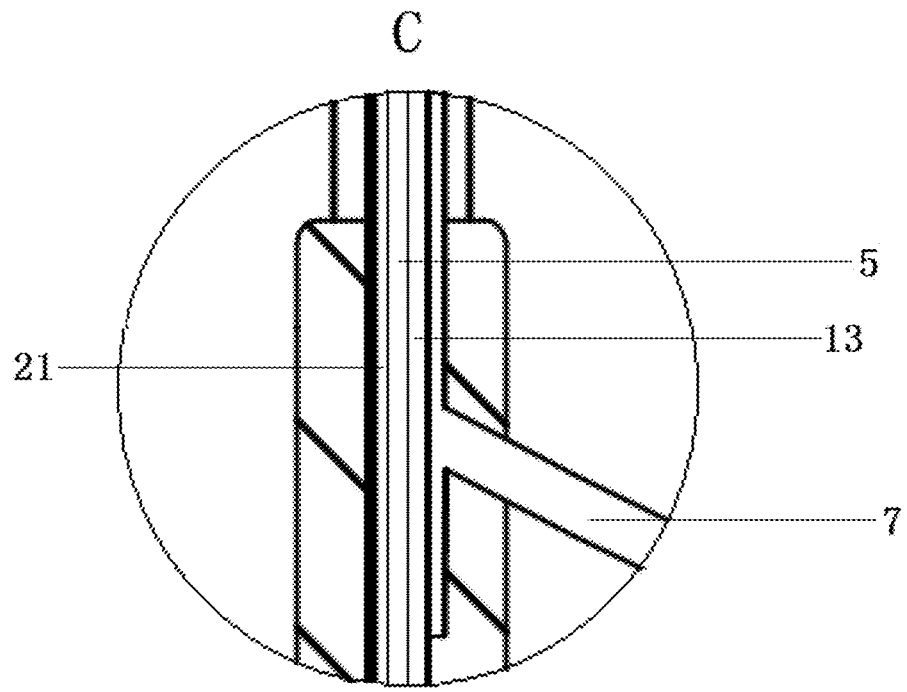
FIG. 5 is a local enlarged view of part C in FIG. 2.

In the drawings, the following reference numbers are used: 1. Balloon; 2. Canula; 3. First joint; 4. Needle tube; 4.1. Tapered head; 5. Image acquisition device; 6. Second axial through hole; 7. Water injection tube; 8. Second joint; 9. Fourth joint; 10. Handle; 10.1. First cylindrical holder; 10.2. Second cylindrical holder; 10.3. Tapered holder; 11. Fluid injection tube; 13. First channel; 14. Clamping part; 15. Annular circumferential surface; 16. First welding part; 17. Second first welding part; 18. Sheath; 19. Instrument delivery pipe; 20. Third joint; and 21. Second channel.

DETAILED DESCRIPTION

To further illustrate the disclosure, embodiments detailing a device for visible puncture are described below. It should be noted that the following embodiments are intended to describe and not to limit the disclosure.

As shown in FIGS. 1-6, the disclosure provides a device for visible puncture comprising a balloon 1, a canula 2, and a water inlet tube (a fluid injection tube 11). A needle tube 4 is disposed in the needle tube 4. The balloon comprises a first end comprising a first hole and a second end comprising a second hole.

Figure 6:
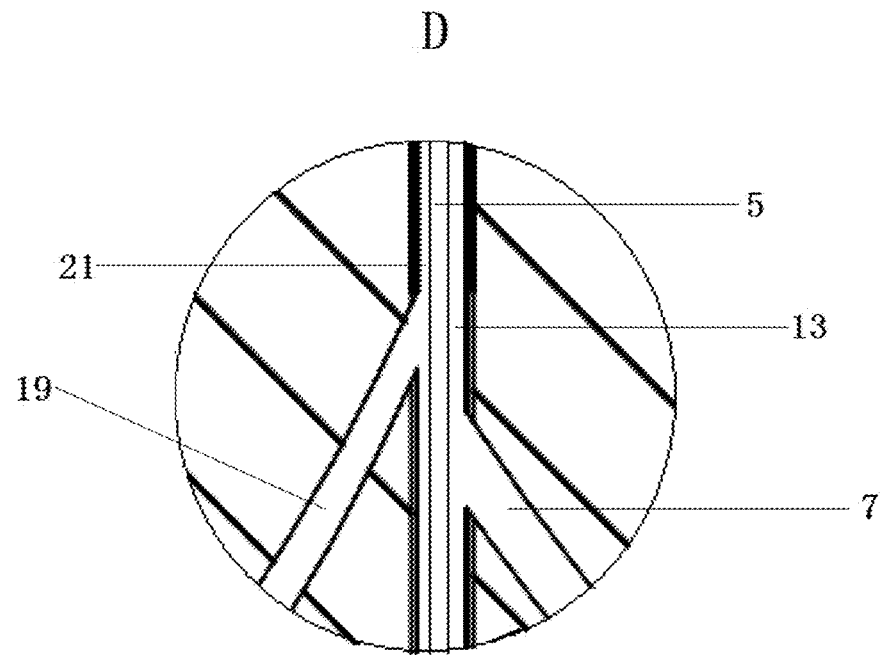
FIG. 6 is a local enlarged view of part D in FIG. 2.

The balloon 1 comprises a first welding part 16 and a second welding part 17 fixed on the outer wall of the front end of the needle tube 4 and the outer wall of the front end of the canula 2, respectively. The rear end of the needle tube 4 passes through the canula 2. The rear end of the canula 2 is in conjunction with the outer wall of the needle tube 4. A fluid channel is disposed between the outer wall of the needle tube 4 and the inner wall of the balloon 1, and between the outer wall of the needle tube 4 and the inner wall of the canula 2. A fluid injection tube 11 is connected to the fluid channel. The fluid injection tube 11 comprises a first joint 3 for fluid injection. The canula 2 comprises a first axial through hole. The needle tube 4 comprises a second axial through hole 6. The needle tube 4 is disposed in the first axial through hole. An image acquisition device 5 (fiber scope, for example) is disposed in the second axial through hole 6. The second axial through hole 6 is connected to a water injection tube 7. The water injection tube 7 is connected to a second joint 8 for water injection. An instrument delivery pipe 19 (a guide wire pipe, for example) is connected to the second axial through hole 6. The water injection tube 7 and the instrument delivery pipe 19 are disconnected in the second axial through hole. The image acquisition device 5 comprises a first outer wall facing the water injection tube and a second outer wall back to back with the first outer wall; a first channel 13 is disposed between an inner wall of the needle tube and the first outer wall of the image acquisition device 5; and the first channel 13 communicates with the water injection tube 7. A second channel 21 is disposed between the inner wall of the needle tube and the second outer wall of the image acquisition device 5; and the second channel 21 communicates with the instrument delivery pipe 19. The device for visible puncture further comprises a handle 10. The instrument delivery pipe 19 comprises a third front end fixed in the handle 10, and a third rear end comprising a third joint 20 for instrument introduction. The rear end of the needle tube 4 is connected to a fourth joint 9 communicating with the image acquisition device 5. As shown in FIG. 6, the front end of the needle tube 4 comprises a tapered head 4.1; the tapered head 4.1 comprises a tapered front end and a flat rear end; the tapered head 4.1 further comprises a central hole communicating with the second axial through hole 6 and the central hole has the same diameter as the second axial through hole 6; the first end of the balloon is fixed on the flat rear end of the tapered head 4.1, and an outer diameter of the flat rear end of the tapered head 4.1 is the same as an outer diameter of the first end of the balloon 1. The tapered head 4.1 is a part of the needle tube 4 or is soldered on the needle tube 4.

In certain embodiments, the fiber scope (the image acquisition device) is integrated with or independent from the needle tube 4. When the fiber scope is integrated with the needle tube 4, the front end of the image acquisition device 5 is fixed on the inner wall of the needle tube, and the rear end passes through the second axial through hole 6 and the fourth joint 9. There is a gap between the fiber scope and the water outlet of the water injection tube 7. When the fiber scope is independent from the needle tube, when in use, the fiber scope is inserted into the needle tube 4 via the fourth joint 9 to observe the puncture position, and pull out after the operation.

As shown in FIGS. 2-6, the rear end of the canula 2 and the rear end of the needle tube 4 are fixed in the handle 10. The rear end of the needle tube 4 passes through the handle 10 and is connected to the fourth joint 9. One end of the fluid injection tube 11 is connected to the canula 2, and the other end passes through the handle and is connected to the first joint. One end of the water injection tube 7 is connected to the needle tube 4, and the other end passes through the handle and is connected to the second joint 8.

In certain embodiments, the handle comprises a first cylindrical holder 10.1, a second cylindrical holder 10.2 coaxially fixed on the first cylindrical holder, and a tapered holder 10.3 coaxially fixed on the second cylindrical holder; a diameter of the second cylindrical holder is larger than a diameter of the first cylindrical holder; a transition section of the second cylindrical holder and the tapered holder 10.3 comprises a clamping part 14 shaped like a finger (this is convenient for a user to hold the device); and the tapered holder 10.3 comprises a rear end having an annular circumferential surface 15 (this is convenient for the operator to hold, increasing the friction force of hands, thus ensuring the stable operation of the medical staff).

The usage method of the device for visible puncture is described as follows:

1) The fiber scope is inserted into the second axial through hole 6 and locked in a target location. The sheath 18 is disposed on the needle tube 4 (if the fiber scope is integrated with the needle tube 4, only need to dispose the sheath on the needle tube 4). The sheath 18 is a hollow pipe; when the balloon 1 is filled with a fluid and expanded to show a maximum section width, and the maximum section width of the balloon 1 is smaller than the inner diameter of the sheath 18.
2) The optical fiber of the fiber scope is connected to a camera system until a normal image can be seen on the display.
3) The device for visible puncture is held by hand. Under B-ultrasound equipment, the needle tube 4, the balloon 1, and canula 2 cooperate with each other for puncture. The needle tube 4 reaches the renal pelvis and renal calices through the epidermis. The renal collection system can be seen on the optical fiber mirror. If the imaging is not clear, a small amount of physiological saline can be injected into the needle tube 4 through the second joint 8 to clear the vision so as to determine the puncture position of the renal collection system.
4) When the needle tube 4 reaches the target position, normal saline is injected into the balloon 1 through a water filling connector to expand the balloon 1 using a syringe. When the pressure on the syringe reaches the set pressure (25 atmospheres), stop filling water and hold for 30 seconds. The sheath 18 is pushed forward along the needle tube 4 and sheathed on the balloon 1. Thereafter, the water in the balloon 1 is drained and the balloon is taken out. Thus, the sheath 18 stays in an expanded channel completed by the balloon 1, so that the expanded state is remained, that is to say, the working channel of percutaneous renal surgery is established.

In 3), when the needle tube 4 reaches the target position, the guide wire is introduced into the second axial through hole 6 via the third joint 20 and the instrument delivery pipe 19. After 4) is completed, only the sheath 18 and the guide wire are remained, and other parts are pulled out. The guide wire is used for introduction of subsequent surgical instruments.

The device for visible puncture incorporates the needle tube 4 and the balloon 1, and the fiber scope is built-in in the device or introduced temporarily as needed. Using the device, the puncture position can be clearly observed thus improving the operation accuracy. Compared with a convention puncture device which involves the withdrawal of the puncture needle, the placement and stabilization of the guide wire, the withdrawal of the sheath of the puncture needle, the expansion of the sheath core along the guide wire, and the withdrawal of the sheath core, the operation of the device of the disclosure is simple. The operations of the puncture and the expansion are fulfilled in the same device, without the operations of withdrawal or replacement of the guide wire, thus saving the usage of consumable items, reducing the operation time, reducing the risk of surgery, reducing the cost of surgery, and reducing the pain of patients. During the expansion process, the state of the renal collection system can be monitored through the fiber optic mirror to reduce the risk of bleeding. The device of the disclosure can be applied in general surgery, neurosurgery, urology, hepatobiliary surgery, gynecology and so on.

It will be obvious to those skilled in the art that changes and modifications may be made, and therefore, the aim in the appended claims is to cover all such changes and modifications.

What is claimed is:

1. A device, comprising:
   a balloon, the balloon comprising: a first end comprising a first hole, and a second end comprising a second hole;
   a canula comprising a first axial through hole;
   a needle tube comprising a second axial through hole, the needle tube being disposed in the first axial through hole;
   an image acquisition device disposed in the second axial through hole; and
   a fluid injection tube;
   wherein:
   the balloon is axially disposed on the canula; the first end of the balloon is disposed on an outer wall of a front end of the needle tube, and the second end of the balloon is disposed on an outer wall of a front end of the canula;
   a fluid channel disposed between the outer wall of the needle tube and an inner wall of the balloon, and between the outer wall of the needle tube and an inner wall of the canula; and
   the fluid injection tube is connected to the fluid channel.

2. The device of claim 1, further comprising a water injection tube communicating with the second axial through hole.

3. The device of claim 2, further comprising an instrument delivery pipe communicating with the second axial through hole; wherein the water injection tube and the instrument delivery pipe are disconnected in the second axial through hole.

4. The device of claim 3, further comprising a handle; wherein the rear end of the canula and a rear end of the needle tube are fixed in the handle; the handle comprises a first cylindrical holder, a second cylindrical holder coaxially fixed on the first cylindrical holder, and a tapered holder coaxially fixed on the second cylindrical holder; a diameter of the second cylindrical holder is larger than a diameter of the first cylindrical holder; a transition section of the second cylindrical holder and the tapered holder comprises a clamping part shaped like a finger; and the tapered holder comprises a rear end having an annular circumferential surface.

5. The device of claim 4, wherein the fluid injection tube comprises a first front end fixed in the handle, and a first rear end comprising a first joint for fluid injection; the water injection tube comprises a second front end fixed in the handle, and a second rear end comprising a second joint for water injection; the instrument delivery pipe comprises a third front end fixed in the handle, and a third rear end comprising a third joint for instrument introduction; and the rear end of the needle tube is connected to a fourth joint communicating with the image acquisition device.

6. The device of claim 5, wherein the image acquisition device comprises a first end fixed on the inner wall of the needle tube, and a second end passing through the fourth joint.

7. The device of claim 1, wherein the balloon comprises a first welding part and a second welding part fixed on the outer wall of the front end of the needle tube and the outer wall of the front end of the canula, respectively.

8. The device of claim 1, further comprising a sheath disposed on the balloon; wherein the sheath comprises a third axial through hole; when the balloon is filled with a fluid and expanded to show a maximum section width, and the maximum section width is smaller than an inner diameter of the sheath.

9. The device of claim 1, wherein the front end of the needle tube comprises a tapered head; the tapered head comprises a tapered front end and a flat rear end; the tapered head further comprises a central hole communicating with the second axial through hole and the central hole has the same diameter as the second axial through hole; the first end of the balloon is fixed on the flat rear end of the tapered head, and an outer diameter of the flat rear end of the tapered head is the same as an outer diameter of the first end of the balloon.

* * * * *